United States Patent [19]
Summers et al.

[11] Patent Number: 5,980,551
[45] Date of Patent: Nov. 9, 1999

[54] COMPOSITION AND METHOD FOR MAKING A BIODEGRADABLE DRUG DELIVERY STENT

[75] Inventors: David P. Summers, Montgomery, Tex.; Jackie R. See, Las Vegas, Nev.

[73] Assignee: Endovasc Ltd., Inc., Montgomery, Tex.

[21] Appl. No.: 08/797,743

[22] Filed: Feb. 7, 1997

[51] Int. Cl.⁶ ............................................... A61M 29/00
[52] U.S. Cl. ................................................ 606/194; 623/1
[58] Field of Search .................................... 606/154, 194, 606/195, 198; 623/1; 424/450

[56] References Cited

U.S. PATENT DOCUMENTS

| | | | |
|---|---|---|---|
| 5,082,664 | 1/1992 | Lenk et al. | 424/450 |
| 5,464,450 | 11/1995 | Buscemi et al. | 606/154 |
| 5,624,411 | 4/1997 | Tuch | 623/1 |
| 5,674,242 | 10/1997 | Phan et al. | 606/195 |
| 5,697,967 | 12/1997 | Dinh et al. | 623/1 |

OTHER PUBLICATIONS

Ganesh Rajasubramanian et al., Fabrication of Resorbable Microporous Intravascular Stents for Gene Therapy Applications, ASAIO Journal 1994, pp. M584–M589.

Neil P. Desai et. al., Solution Technique to Incorporate Polyethylene Oxide and Other Water Soluble Polymers into Surfaces of Polymeric Biomaterials, 1990.

Yasuhide Nakayama, Microporous Polymer Surfaces Prepared by an Excimer Laser Ablation Technique, ASAIO Journal 1994.

Michel Henry, MD et al., Clinical Experience with a New Nitinol Self–Expanding Stent in Peripheral Arteries, J. Endovasc Surg, 1996, pp. 369–379.

Armin Bolz, PhD et al., Coating of Cardiovascular Stents with a Semi–Conductor to Improve Their Hemolompatibility, Tex Heart Inst J, 1996, pp. 162–166.

Yoshiyuki Murakami et al., Effect of the Molecular Weight of Water–Soluble Polymers on Accumulation at an Inflammatory Site Following Intravenous Injection, Drug Delivery, 1996, pp. 231–238.

*Primary Examiner*—Michael Buiz
*Assistant Examiner*—Julian W. Woo
*Attorney, Agent, or Firm*—Nick A. Nichols, Jr.

[57] ABSTRACT

A stent or vascular graft for supporting a blood vessel or organ lumen is coated with a biodegradable, resorbable and hemocompatible surface substrate. Biologically active microspheres which controllably release the biologically active agent into the vessel wall or organ to inhibit restenosis of the stent is embedded in the stent substrate. The biologically active microspheres include encapsulated PGE1 in a water soluble polyethylene glycol mix, which over a period of time dissolves and releases the PGE1 into the vessel wall or organ.

10 Claims, 1 Drawing Sheet

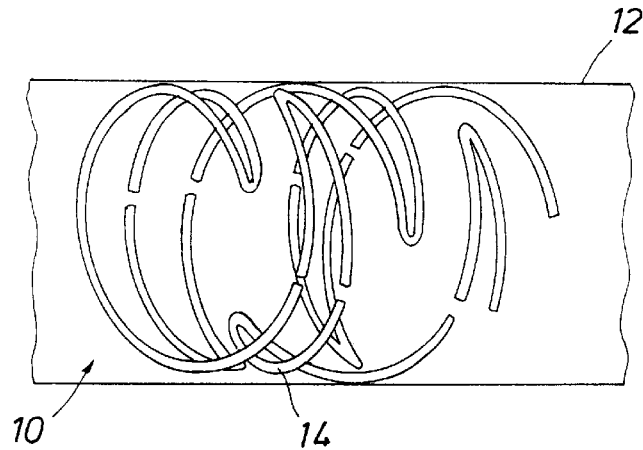
FIG. 1
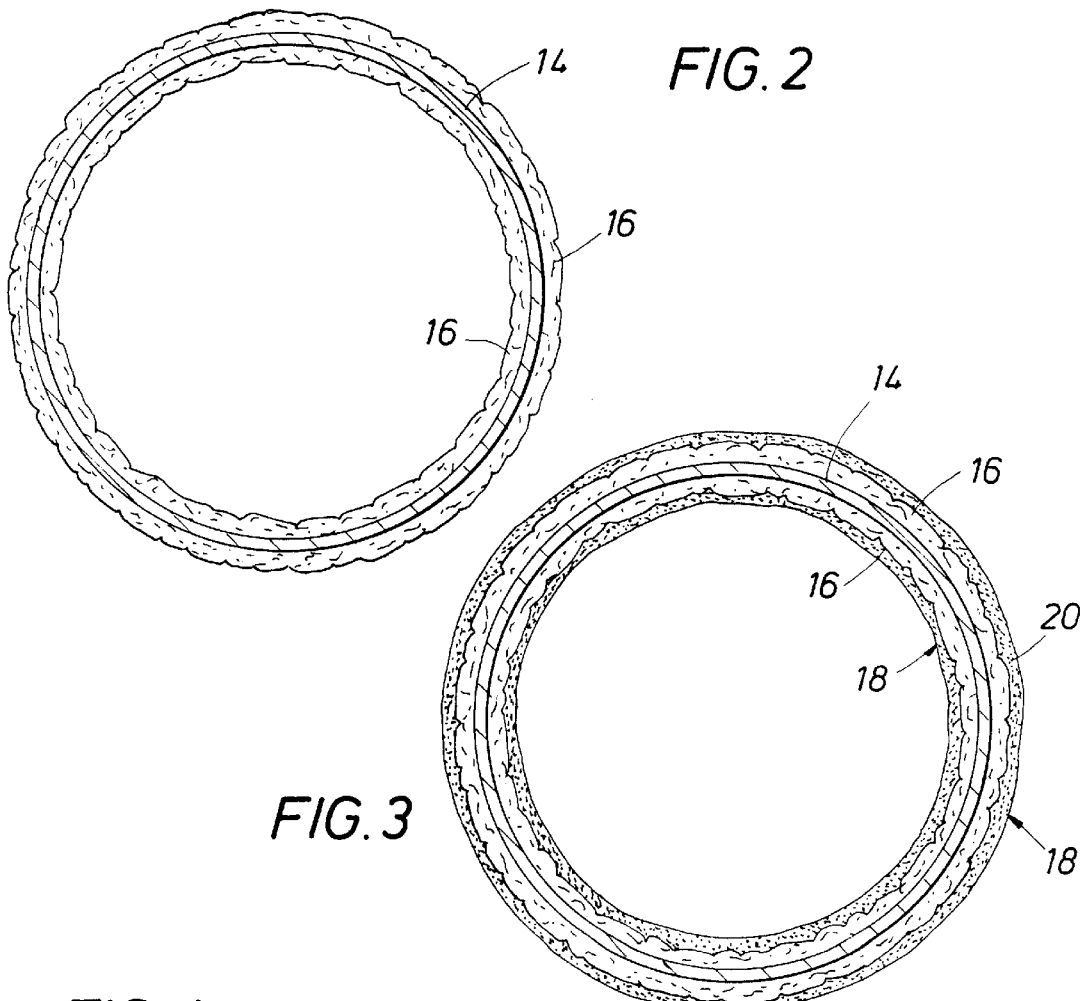
FIG. 2
FIG. 3
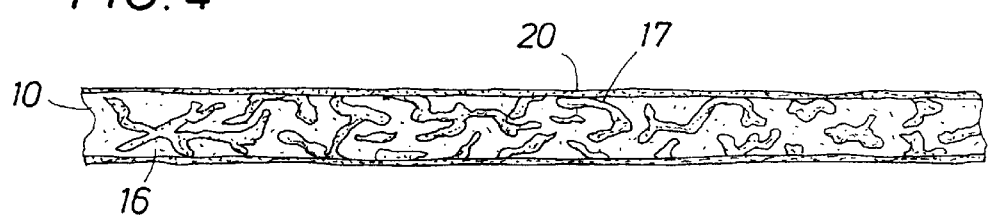
FIG. 4

COMPOSITION AND METHOD FOR MAKING A BIODEGRADABLE DRUG DELIVERY STENT

BACKGROUND OF THE INVENTION

The present invention relates to biodegradable drug delivery stents, particularly stents coated with a biocompatible substance impregnated with antithrombocyte/antithrombin agents released over a period of time to reduce or eliminate restenosis in the blood vessel.

Percutaneous endovascular stenting was conceived in the late 1970's as a way to prevent both acute occlusion and late restenosis after catheter intervention, but initial clinical results of coronary stenting in 1987 were plagued by high (>20%) acute and subacute thrombosis and were restricted to use as "bailout" for threatened or acute vessel closure. In recent years, stent outcomes have improved progressively with better placement techniques and in 1995, an estimated 700,000 stents were implanted world-wide. Recent STRESS (Stent Restenosis Study, 1994) and BENESTENT trials (Belgium-Netherlands Stent, 1995) demonstrated that stenting of native coronary arteries is associated with greater procedural success. The trials demonstrated that fewer acute, adverse events and less angiographic restenosis and lower rates of 8-months target vessel revascularization occurred than in conventional balloon angioplasty. Stents are now used as primary treatment and secondary bailout.

Despite their utility, stents have been plagued by two problems, namely, acute occlusion due to thrombosis and persistent occurrence of restenosis. Recent studies show that coronary stenting results in significant platelet, polymorphonuclear leukocyte, and macrophage activation, as well as activation of the coagulation pathway which induce clots despite passivation and/or anti-coagulation treatment of the stent surface. This limitation relates to the surface exposure of adhesion receptors on activated platelets to the foreign surface of the stent, producing the aforementioned thrombogenic activity that must be countered with intense anticoagulation regimens. Subacute stent thrombosis occurs most frequently during the first few days after implantation and almost always in the first two weeks. Thereafter, neointimal cells including proliferating smooth muscle cells from the vessel wall and endothelial hyperplastic cells encompass the stent surface and ameliate the risk of stent thrombosis.

Notwithstanding the above, vascular stents have proven to be of great therapeutic value in the treatment and prevention of complications relating to percutaneous transminal coronary angioplasty (PTCA). Mechanical problems of the vessel wall, i.e., vessel dissection, the most frequent cause of acute closure in about 25% of patients leading to acute myocardial infarction associated with PTCA, is virtually eliminated with stents. However, such major acute and chronic adverse events persist in more than 25% of patients. One of the most important causes is the trombogenicity of the stent itself. Despite increased biocompatibility currently available, stents have less than hemocompatibility and are further limited because of late incidence in virtually all stents of restenosis, potentially fatal late complications from clotting and an aggressive type of in-stent restenosis resistant to therapy. In-stent restenosis is much more difficult to treat than PTCA restenosis, frequently resulting in coronary artery bypass grafting (CABG).

In addition to the morbidity and mortality, stents are more expensive than PTCA and require longer hospitalization in order to provide anticoagulant and antispasm therapy due to the induction of thrombogenicity and spasm by the stent, a foreign object, introduced into the vascular wall. The heavy anticoagulation required can produce major bleeding events and vascular complications, often necessitating surgical intervention.

What is desired is a stent coating of antithrombolic, antispasm agents which will biodegrade over time, eluting drugs into the vessel wall to inhibit these complications and obviating systemic oral or intravenous or intraarterial drug delivery with heightened cost and side effect profile. PGE1 is the ideal antithrombolic agent and antispasmodic agent, which also has antiproliferative effects on the smooth muscle cell (SMC). In addition, PGE1 is very effective in antiplatelet activation and deposition, and produces blocking effects on leukocyte adhesion molecules through the lipoxygenase and leukotriene pathway and blocks macrophage migration and aggregation at the injury site.

Much work has been done to both passivate and/or biologically enhance the surface properties of stents so as to reduce the need for anticoagulants and the like. For example, Bolz, et al., described a process for coating stents with a semi-conductor (Bolz, A., et al, *Coating of Cardiovascular Stents with a Semi-Conductor to Improve Their Hemocompatibility*, Tex. Heart Inst. Jour. 1996;23:162–6) which provided electrical passivation of the surface charge of stents thereby neutralizing the attraction of coagulating proteins. Other investigations have grafted both active and neutral substances to stents, such as hirudin or neutral collagen, in attempts to ameliate coagulation. (Prietzel, K. et al. *Inhibition of Neointimal Proliferation with a Novel Hirudin/Prostacyclin Analog Eluting Stent Coating in an Animal Overstrech Model*, Abstract, Circulation, Supplement 1, Vol. 94, No. 8, Oct. 15, 1996, p. 1–260); U.S. Pat. No. 5,342,387, Summers, *Artificial Support for a Blood Vessel*. These coatings have proven less than successful in ameliating the total problem. Two factors, cellular proliferation within the stent lumen itself and late vessel wall remolding, remain unsolved.

Restenosis within and around the stent is a process of chronic new endothelial and medial cellular growth, and remolding of the vessel after intervention which usually occurs by the third month postintervention. Restenosis is a continuum of extracellular matrix rebuilding after stretching, which continues from the time of PTCA, peaking at three months and unusually terminating after six months. Although percutaneous delivery of stents has been shown to slightly reduce the frequency of restenosis as compared to PTCA, when such lesions do occur within a stent, they have been considered to result from intimal proliferation with smooth muscle cells, the predominate cell type, and are resistant to treatment, since PTCA is generally precluded and rotational atherectomy or CABG usually required. Therefore, it is obvious that stent occlusion is a two-phase problem having an acute phase in which platelet, leukocyte, macrophage aggregation, and thrombosis is the primary concern and a chronic and late-phase problem in which intimal in-stent proliferation and vessel wall remolding is the primary concern. It is, therefore, an object of the instant invention to overcome both acute and chronic concerns with the foregoing invention.

Since most cellular interactions are protein mediated, the prevention or reduction in protein absorption to a stent would serve to prevent cellular attachment and subsequent events that may otherwise render the stent materials biocompatible but in doing so, produce the unwanted adverse effects of not coating the stent. A stent coated with a composition of both biocompatible agents and drug eluting systems such as PGEI to retard initial harmful vascular cellular and thrombosis mechanisms, while allowing normal subsequent acceptance of the stent by the vessel wall by orderly vascular cell covering with endothelial and medial cells, and compatible treatment for post-PTCA complications would be desirable.

Poly-L-lactic acid (PLLA)/Poly-caprolactone (PCL) blends of aliphatic polyester polymers have proven to be both biodegradable, resorbable and hemocompatible. Depending on the ratio of PLLA to PCL, these coatings can provide a benign substrate that provides a microporous structure that can efficiently be impregnated with biologically active microsphere such as liposomes in the range of 20 nm to 1000 nm.

It is therefore an object of the invention to provide a stent having a PLLA/PCL coating substrate formed thereon and impregnating the coating substrate with biologically active microspheres.

It is a further object of the invention to provide a stent coating whereby the coating substrate is coated with a layer of PGE1-encapsulated liposomes which release PGE1 over an extended period of time.

SUMMARY OF THE INVENTION

The present invention provides a stent coated with a biodegradable, resorbable and hemocompatible surface substrate. The substrate is impregnated with biologically active microspheres which controllably release the biologically active agent into the vessel wall to inhibit restenosis of the stent. The biologically active microspheres include encapsulated PGE1 in a water soluble polyethylene glycol mix, which over a period of time dissolves and releases the PGE1 into the vessel wall.

BRIEF DESCRIPTION OF THE DRAWINGS

So that the manner in which the above recited features, advantages and objects of the present invention are attained can be understood in detail, a more particular description of the invention, briefly summarized above, may be had by reference to the embodiments thereof which are illustrated in the appended drawings.

It is noted, however, that the appended drawings illustrate only typical embodiments of this invention and are therefore not to be considered limiting of its scope, for the invention may admit to other equally effective embodiments.

FIG. 1 is an enlarged view of two loops of a double-helix stent according to the invention located within a blood vessel;

FIG. 2 is a sectional view of the stent of the invention depicting the substrate coating formed on the surface of the stent;

FIG. 3 is a sectional view of the stent of the invention depicting the substrate coating and encapsulated biologically active microspheres formed on the surface of the stent; and FIG. 4 is a is an enhanced microscopic view of the stent substrate coating of the invention.

DETAILED DESCRIPTION OF A PREFERRED EMBODIMENT

Referring first to FIG. 1, the coated stent of the invention, generally identified by the reference numeral 10, is shown located in a blood vessel 12. The stent 10 is shown as having a double-helix wire configuration positioned in a blood vessel for illustrative purposes. It is understood that the stent 10 may comprise other configurations and be positioned in any organ requiring support to open a lumen or passageway without departing from the scope of the present invention. Referring still to FIG. 1, the stent 10 is located in the vessel 12 in the region where the vessel wall has collapsed and requires support to maintain the vessel 12 in an open condition. While it has been shown that stents have great therapeutic value, stents have suffered from unacceptable hemocompatibility which typically results in restenosis of the vessel 12 which is much more difficult to treat.

Referring now the FIG. 2, stent 10 of the invention comprises a wire 14 which, as noted above, is configured in the shape of a double-helix. The wire 14 is coated with a substrate 16. The substrate 16 encapsulates the stent wire 14 and comprises, in the preferred embodiment, a 50:50 combination of PLLA/PCL which is swollen in 40% trifluoacetic acid with polyethylene oxide (PEO) to first open the pores of the substrate 16 for loading of microspheres or liposomes in microspherical geometries (according to Rajasubramanian, et al, *Fabrication of Resorbable Microporous Intravascular Stents For Gene Therapy Applications,* ASAIO Journal, 1994, M584–89). The acidic combination etches the skin surface and the pore walls of the substrate 16, rendering the polymer surfaces more hydrophilic. The etched pores 17 of the substrate 16 have an irregular pore surface and define a mean pore size of 150–200 nm long axis and 50–75 nm short axis. The porosity of the substrate 16 is in the range of 19% to 44%.

After swelling, the surface of the substrate 16 is coated with a slurry of PGEl-encapsulated liposomes in a polyethylene glycol (PEG) mix 18 having a neutral pH which first fills and then collapses the pores 17 of the substrate 16 about the embedded liposomes 20, as best shown in FIG. 4. The pores 17 are filled with liposomes 20 of 100 nm to 200 nm diameters, providing a mean average of about 1000 liposomal microspheres per pore. What remains then is a modified surface coating, producing biocompatible, cell-nonadhesive surface of PEG and lyophilized liposomal microspheres. PEG itself has been shown to have protein-repelling activity when immobilizing on a surface due to its hydrophilicity, chain mobility, and lack of ionic charge. Since PEG is water-soluble, platelet adhesion and thrombus formation is further limited by a continuous semi-dissolved molecular disassociation which actually increases the hydrophilicity of the stent substrate 16, making surface adhesion on the stent 10 even more difficult.

After placement of the stent 10 in the vessel 12, the water-soluble surface polymers of PEG begin to dissolve thereby exposing the surface embedded liposomes 20. The liposomes 20 are exposed in stages; the first exposure being those on or close to the surface coating of the substrate 16. The liposomes 20 embedded within the pores 17 of the substrate 16 remain inactivated until both the PEG overlay mixture 18 and the portion of PLLA/PCL encompassing the closed pores 17 of the substrate 16 has been resorbed and thereby releasing the liposomes 20, a process that may continue over a period of time up to six months.

Once the outer coating of the substrate 16 is "dissolved" and upon activation, the liposomes 20 release their biologically active agent by leaking out the liposomes 20 into the vessel wall 12. In the preferred embodiment of the present invention, the active agent encapsulated within the liposomes 20 is prostaglandin E1 (PGE1), a natural-occurring fatty acid of the cyclopentenone family.

The release of the liposomal PGE1 produces a secondary effect that is both synergistic and antagonistic. It is synergistic with the PEG, in that the PEG tends to accumulate at the injured tissue and with long chain lengths further inhibits cellular interactions at the polymer surface, but in addition, the timed release of PEG1 produces powerful chronic antagonistic chemotaxis to thromboxane and leukotriene actions on the platelets and injured vessel wall while modulating the proliferation of smooth muscle cells (SMC) and extracellular matrix within the media of the blood vessel 12. This two-stage process continues to produce inhibition of protein absorption and hence cellular interactions at the biomaterial surface while releasing powerful inhibitions of platelet aggrandizement and modulators of cell growth in the region of the vessel wall 12 where the stent 10 is located. The protein inhibiting action of the biologically active agent continues over a predetermined period of weeks or months or until endothelialization of the biosurface is complete. Of particular note, the labile PEG end-groups on these modified surfaces can be made to serve as attachment sites for suitable biospecific peptides that result in a surface that could potentially adhere to only one particular cell type, such as endothelial cells in the case of stents or vascular grafts.

While a preferred embodiment of the invention has been shown and described, other and further embodiments of the invention may be devised without departing from the basic scope thereof, and the scope thereof is determined by the claims which follow.

We claim:

1. A stent for supporting a blood vessel, comprising:
   (a) a stent body;
   (b) a biodegradable, porous stent substrate swelled in 40% trifluoacetic acid with polyethylene oxide applied on said stent body, wherein the pores of said stent substrate are opened upon swelling said stent substrate; and
   (c) a polymer mixture coating said stent substrate, said polymer mixture including biologically active microspheres, and wherein said polymer mixture fills and collapes the pores of said stent substrate.

2. The stent of claim 1 wherein said substrate comprises one or more layers of a resorbable PLLA/PLC mixture encapsulating said stent body.

3. The stent of claim 2 wherein said water soluble polymer mixture comprises a slurry of polyethylene glycol (PEG) and liposomes carrying a biologically active agent.

4. The stent of claim 1 wherein said stent substrate comprises a Poly-L-lactic acid/Polycaprolactone mixture encapsulating said stent body, and wherein said polymer mixture comprises a Polyethylene glycol/lyophilized liposome surface coating on said stent body, and wherein the liposomes in said surface coating range in average diameter from about 100 nm to 200 nm.

5. The stent of claim 2 wherein said stent substrate and said polymer mixture are water soluble and resorbable, providing a continuous and gradual release of prostaglandin encapsulated in said biologically active microspheres.

6. The stent of claim 1 wherein the pores of said stent substrate define an irregular pore surface for releaseably retaining said biologically active microspheres, and wherein said microspheres contain prostaglandin E1 encapsulated in said microspheres.

7. The stent of claim 6 wherein the pores of said stent substrate have a mean pore size of 150 nm to 200 nm long axis and 50 nm to 75 nm short axis.

8. The stent of claim 7 wherein said microspheres release prostaglandin E1 at a controlled rate for up to six months.

9. The stent of claim 1 wherein said stent substrate has a porosity of 18% to 45%.

10. A method of modifying cellular response in a blood vessel or organ to a disease, injury or foreign body, comprising the steps of:
    a) forming a water soluble and resorbable hemocompatible stent coating;
    b) swelling said stent coating in 40% trifluoacetic acid with polyethylene oxide to open the pores of said stent coating;
    c) embedding microspheres having a biologically active agent encapsuled in said microspheres in said stent coating;
    d) applying said stent coating on a stent body;
    e) positioning said stent body in the blood vessel or organ; and
    f) controllably releasing said biologically active agent into the blood vessel wall or target organ.

* * * * *